(12) United States Patent
Ito et al.

(10) Patent No.: US 6,868,308 B2
(45) Date of Patent: Mar. 15, 2005

(54) OPERATION GUIDANCE METHOD OF CLINICAL SYSTEM

(75) Inventors: Eitaro Ito, Kokubunji (JP); Kazuhisa Machida, Kawasaki (JP); Susumu Kai, Hitachinaka (JP); Yoshimitsu Takagi, Hitachinaka (JP); Yasuhiro Higuchi, Funabashi (JP)

(73) Assignee: Hitachi, Ltd., Tokyo (JP)

( * ) Notice: Subject to any disclaimer, the term of this patent is extended or adjusted under 35 U.S.C. 154(b) by 514 days.

(21) Appl. No.: 09/935,846

(22) Filed: Aug. 24, 2001

(65) Prior Publication Data

US 2002/0031444 A1 Mar. 14, 2002

(30) Foreign Application Priority Data

Sep. 11, 2000 (JP) ........................................ 2000-275218

(51) Int. Cl.[7] .......................... G05B 21/00; G01N 35/00
(52) U.S. Cl. .......................... 700/266; 700/17; 700/83; 345/961; 345/967; 436/43; 422/62; 422/67; 422/68.1
(58) Field of Search ............................... 436/43, 47, 48, 436/50; 422/62, 63, 65, 67, 68.1; 435/287.1, 287.3; 700/17, 83, 266; 345/961, 965, 967

(56) References Cited

U.S. PATENT DOCUMENTS 6,442,440 B1 * 8/2002 Miller ......................... 700/83
6,602,469 B1 * 8/2003 Maus et al. ................. 422/68.1

FOREIGN PATENT DOCUMENTS

| JP | 08-101204 | * | 4/1996 |
| JP | 09-072910 | * | 3/1997 |
| JP | 09-072911 | * | 3/1997 |

* cited by examiner

Primary Examiner—Maureen M. Wallenhorst
(74) Attorney, Agent, or Firm—Antonelli, Terry, Stout & Kraus, LLP

(57) ABSTRACT

An operation guidance method of clinical system which enables a doctor or nurse unskilled in testing to operate the clinical system without operation error by providing operation guidance. In the system, an initial screen shows numerals 1 to 5 indicating the order of procedure of sample test and character information indicating the contents of works (1 confirmation of sample, 2 confirmation of request, 3 feeding samples, 4 confirmation of result and 5 finish) as contents displayed in an operation menu. When an operator selects a "start" button, display images showing as guidance on the respective works are sequentially displayed. Further, a display image as guidance on arbitrary one of the works may be displayed by selection of one of the works in the operation menu.

12 Claims, 18 Drawing Sheets

1-1 CONFIRMATION OF SAMPLE

CONFIRMATION OF BARCODE

PLEASE CONFIRM AS IF THE BARCODE IS CORRECTLY LABELED

─── SOLUTIONS ───

CASE1 : BARCODE IS NOT PRINTED OUT CORRECTLY
▶ PRINT OUT BARCODE AND LABELED IT

CASE2 : BARCODE IS NOT LABELED CORRECT POSITION
▶ BARCODE MUST BE LABELED IN PARALLEL WITH TUBE RE-LABEL IN CORRECT POSITION

CLOSE

*1-2* CONFIRMATION OF SAMPLE TYPE

CONFIRMATION OF SAMPLE

CONFIRM THE SAMPLE TYPE TO FEED INTO THE SYSTEM

═ DETAIL DESCRIPTION ═══════════════

PLEASE SET THE SAMPLE ON THE RACK WITH FOLLOWING STEP

CLOSE

1-2 SET ON THE RACK

SET A SAMPLE ON THE RACK

SET CONFIRMED SAMPLE ON THE CORRECT RACK

═ DETAIL DESCRIPTION ═

SET CONFIRMED SAMPLE ON EACH RACK

- ■ "WHOLE BLOOD" SAMPLE ON THE GREEN RACK
- ■ "COAGULATION" SAMPLE ON THE GREEN RACK
- ■ "CLINICAL" SAMPLE ON THE LIGHT BLUE RACK

CLOSE

2 PLEASE CONFIRM THE TEST REQUEST

CONFIRM TEST REQUEST

READ BARCODE WITH HANDY BARCODE READER THEN CONFIRM THE TEST REQUEST

--- SOLUTIONS ---

CASE1: NO TEST REQUEST EXISTS

- ▶ DOWNLOAD TEST REQUEST FROM HOST COMPUTER
- ▶ GO TO TEST SELECTION SCREEN THEN MAKE A TEST SELECTION
- ▶ ASK ADMINISTRATOR IN CASE YOU HAVE A TROUBLE

CLOSE

FIG. 13

3 FEED THE SAMPLE

FEED THE SAMPLE

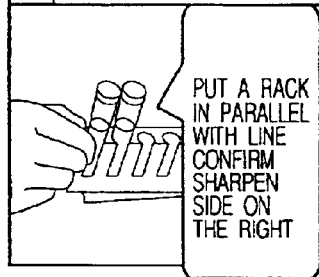

PUT A RACK IN PARALLEL WITH LINE CONFIRM SHARPEN SIDE ON THE RIGHT

FEED A RACK TO THE SYSTEM

--- DETAIL DESCRIPTION ---

SAMPLE FEEDING STEP

■ FEED INTO EMERGENCY PORT
(1) PUT A RACK INTO EMERGENCY PORT CONFIRM DIRECTION
■ FEED INTO SAMPLE FEEDER
(1) SET RACKS ON THE TRAY
(2) SET A TRAY INTO SAMPLE FEEDER
(3) PRESS START BUTTON
(CONFIRM THE RACK IS TRANSFERRED)

CLOSE

*4* CONFIRM THE SAMPLE RESULTS

CONFIRM THE SAMPLE RESULTS

CONFIRM THE DETAIL OF SAMPLE RESULT

=DETAIL DESCRIPTION=

CONFIRM STEP

CLOSE

OPERATION GUIDANCE METHOD OF CLINICAL SYSTEM

BACKGROUND OF THE INVENTION

The present invention relates to an operation guidance method of clinical system, and more particularly, to an operation guidance method of clinical system for automatically performing tests on samples such as blood and urine obtained from a patient in the clinical testing field.

In the clinical testing field, a general clinical system has functions of sorting samples such as blood and urine based on test contents and performing preprocessing, analysis, receipt and the like. The clinical system is entirely controlled from a central control apparatus having a display device, in accordance with operations by an expert laboratory technician.

In this system, if a test is to be performed urgently when the laboratory technician is absent at night time or the like, a doctor or nurse unskilled in testing has to operate the clinical system.

The above conventional clinical system is constructed without consideration of providing operation guidance to such doctor or nurse unskilled in testing in the absence of laboratory technician. Accordingly, operation is difficult to unskilled operator, and further, a wrong test result may be outputted by an operation error.

SUMMARY OF THE INVENTION

The present invention has been made to solve the problems of the above-described prior art, and has its object to provide an operation guidance method of clinical system for providing operation guidance to doctor or nurse unskilled in testing to operate the system in the absence of expert laboratory technician without operation error.

According to the present invention, the foregoing object is attained by providing an operation guidance method of clinical system for testing samples such as blood and urine, comprising the steps of: sorting works to be performed with guidance in accordance with a procedure of operation by a laboratory technician; displaying a menu of sorted works on an initial screen; and providing guidance on operation by sequentially displaying images as operation guidance on respective works in accordance with said procedure of operation. Further, in the operation guidance method of clinical system, if one operation is selected from the work menu, a display image for operation guidance on the work is displayed such that operation is performed in accordance with the display image.

Further, according to the present invention, in the operation guidance method of clinical system, the display image as guidance on the work has an image for operation guidance on one or plural items, and when a displayed item is selected, a display image of ancillary information on the item is displayed as operation guidance.

BRIEF DESCRIPTION OF THE DRAWINGS

FIG. 13 is an example of operation guidance display image (9);

DETAILED DESCRIPTION OF THE PREFERRED EMBODIMENT

A preferred embodiment of the present invention will now be described in detail in accordance with the accompanying drawings.

Figure 1:
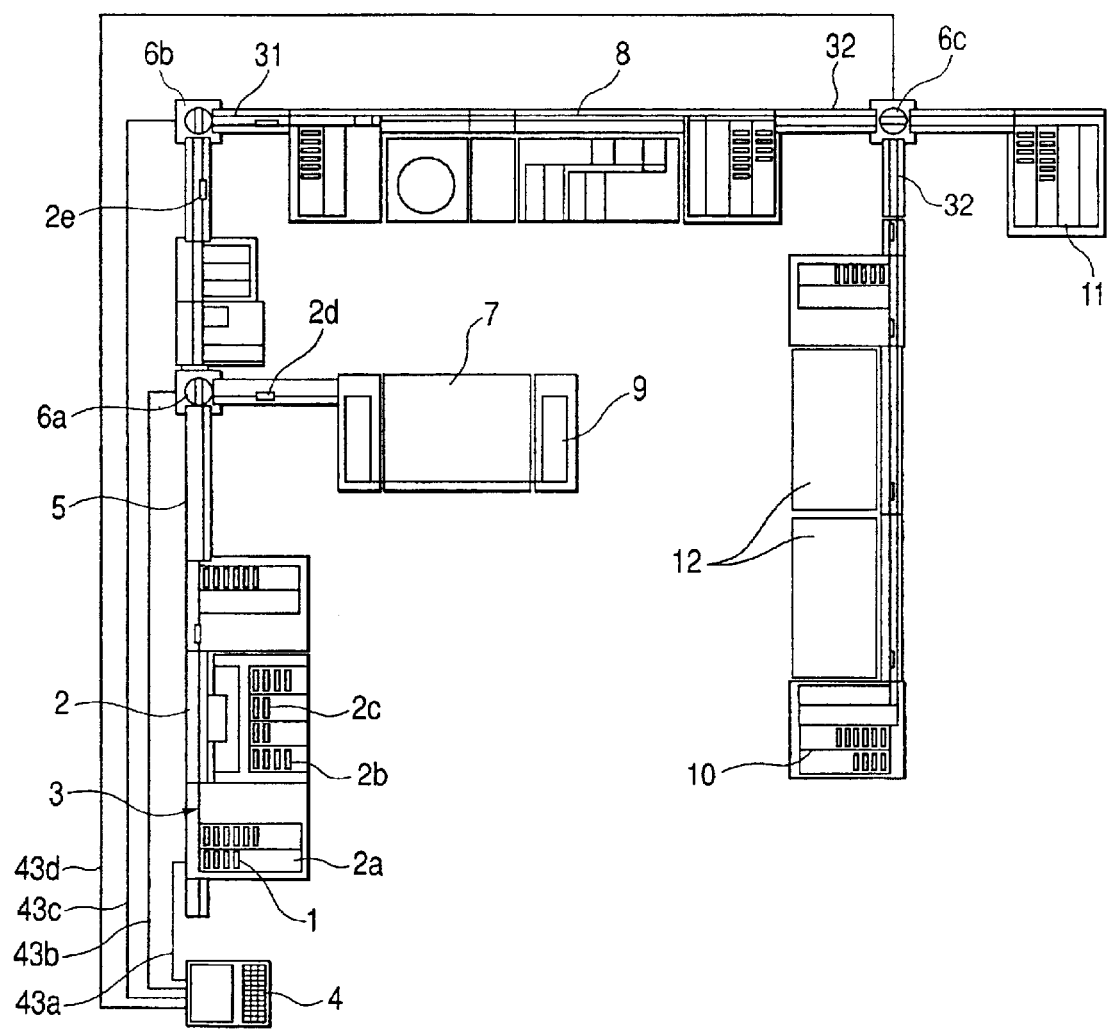
FIG. 1 is a plan view showing the arrangement of clinical system to which the present invention is applied.

FIG. 1 is a plan view showing the arrangement of clinical system to which the present invention is applied. First, the entire construction and the outline of operation of the clinical system will be described with reference to FIG. 1. In FIG. 1, reference numeral 1 denotes a rack; 2, an original sample sorter unit; 2a, an original sample sorter unit rack; 2b and 2c, racks in the original sample sorter unit; 2d and 2e, sorted racks; 3, barcode reader; 4, a control unit; 5 and 32, transportation lines; 6a to 6c, rack turn tables; 7, a blood analyzer; 8, a pre-analyzer modular system; 9 and 10, sample sorters of automation system; 11, a sample sorter of lab automation system; 12, a clinical analyzer; and 43a to 43d, communication cables.

In the construction as shown in FIG. 1, in the clinical system to test samples such as blood and urine, testing/analysis devices such as the blood analyzer 7, the pre-analyzer modular system 8 and the clinical analyzer 12 are connected to the transportation lines 5, 31 and 32 and to the rack turn tables 6a to 6c constructing the clinical system. Further, the system has the control unit 4 that controls destination of the rack 1 to hold samples. The control unit 4, connected to the original sample sorter unit 2 to control the destinations of the racks by communication cables 43a to 43d and to the respective rack turn tables 6a to 6c, receives sample information and controls the destinations of the samples.

In the system, the rack 1 to hold plural containers such as test tubes having collected samples is first set in the original sample sorter unit rack 2a of the original sample sorter unit 2. When placement of the rack 1 on the transportation line 5 is started, the barcode reader 3 reads sample barcodes as sample identification codes attached to the samples and a rack barcode as a rack identification code attached to the rack. Then, positions of samples in the rack are registered into the control unit 4 via the communication cable 43a.

The original sample sorter unit 2 places the samples with different destinations for blood test, biochemical test and the like on the other racks 2b and 2c in the original sample sorter unit 2, and forwards the racks onto the transportation line 5. Thereafter, the sample identification codes or the rack identification codes are read at the rack turn tables 6a to 6c. The rack turn tables 6a to 6c transmit the read information to the control unit 4 via the communication cables 43b to 43c, determine rotation directions upon reception of the destinations of the racks, and transfer the racks to the devices for respective tests. In the example of FIG. 1, the rack 2d is transferred to the blood analyzer 7, and the rack 2e, to the pre-analyzer modular system 8 for centrifuge, stopper opening and the like. The respective racks are finally placed in the sample sorters 9 and 10 in the blood analyzer 7 and clinical analyzer 12 or the sample sorter of lab automation system 11.

The above-described clinical system is controlled by operations by a laboratory technician or the like from the control unit 4 such as a PC having a display device, a mouse, a keyboard and the like. Next, the embodiment of the present invention for operation guidance by using images displayed on the display device will be described in detail with reference to the drawings.

Figure 2:
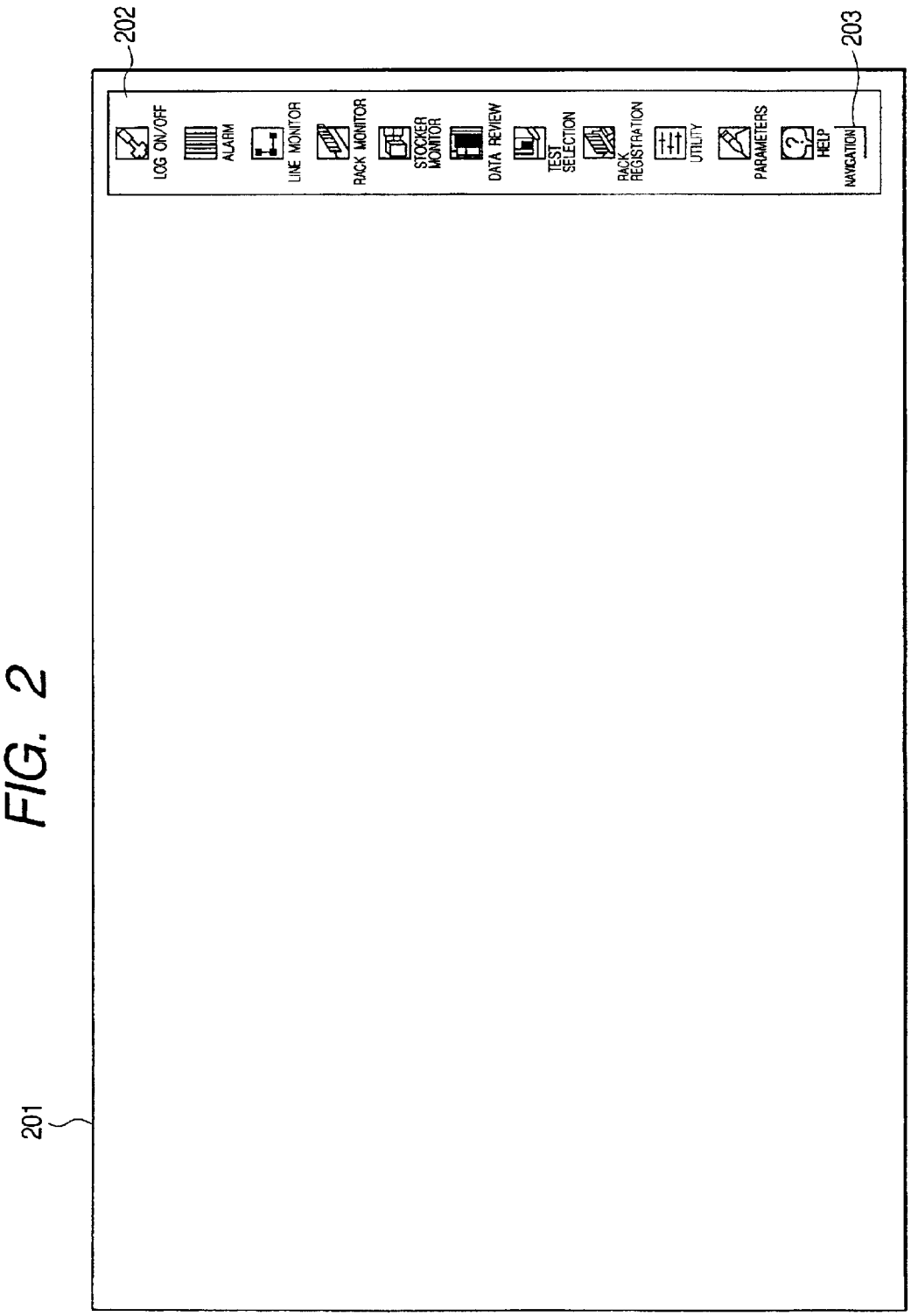
FIG. 2 is an example of initial screen displayed on a display device when an expert laboratory technician operates the clinical system.
Figure 3:
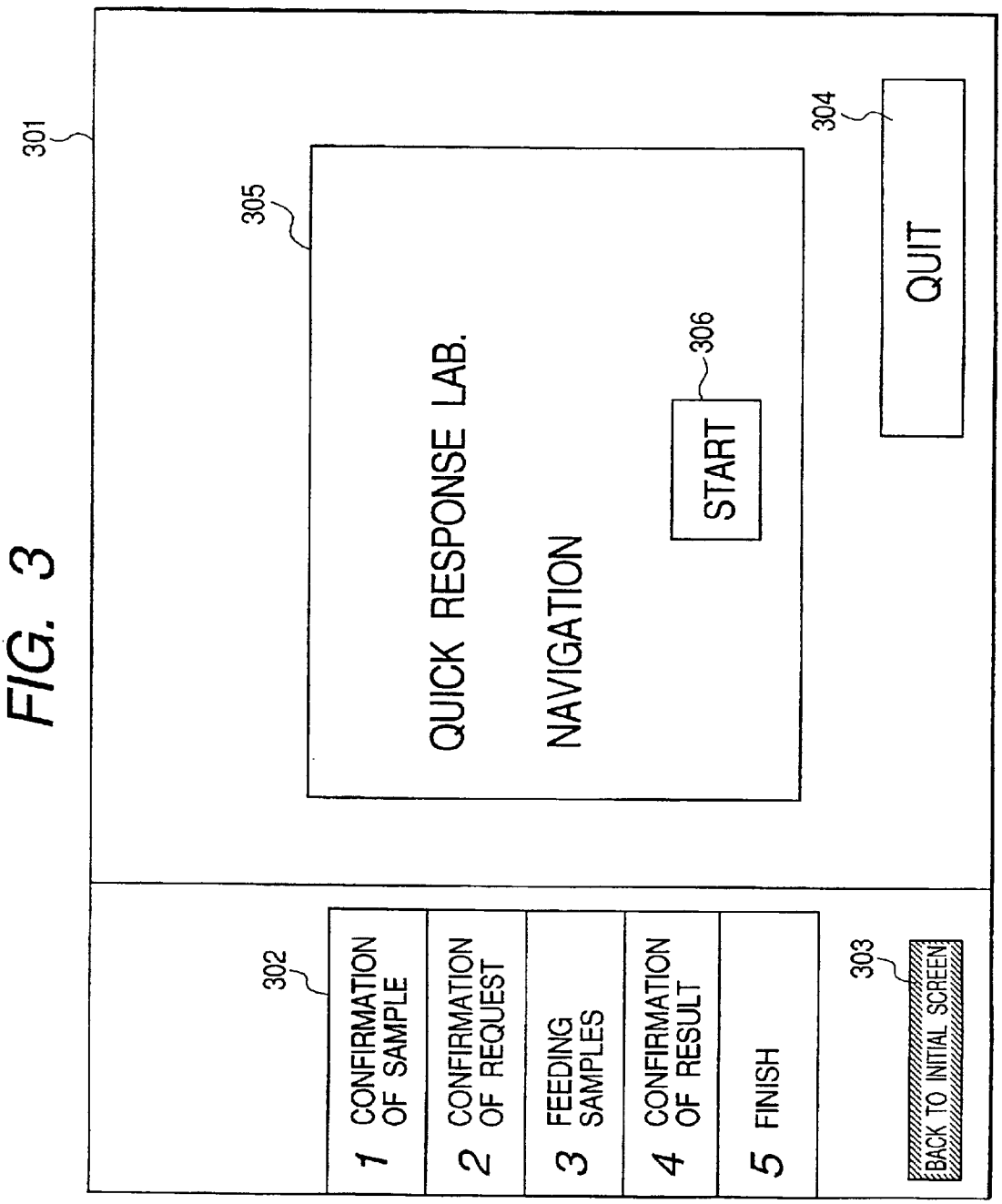
FIG. 3 is an example of initial screen displayed on the display device when a doctor, nurse or the like unskilled in operation operates the clinical system.

FIG. 2 is an example of initial screen displayed on the display device when an expert laboratory technician operates the clinical system. FIG. 3 is an example of initial screen displayed on the display device when a doctor, nurse or the like unskilled in operation operates the clinical system. In FIGS. 2 and 3, numerals 201 and 301 denote initial screens; 202, a task bar; 203, a navigation program icon; 302, an operation menu; 303, a "back to initial screen" button; 304, a "quit navigation" button; 305, a title; 306, a "start" button.

The example of the initial screen 201 in FIG. 2 is an initial screen which can be operated only by the expert laboratory technician displayed in the display device when the laboratory technician operates the clinical system. In this example, nothing is displayed in the central portion of the display screen, however, the name of clinical system, icons of functions of PC other than testing processing and the like may be displayed there. Further, on the right side of the display screen, the task bar 202 showing a number of icons for monitoring of testing device operation, various operations, parameter setup, various test processings is displayed. When the laboratory technician uses the clinical system, the technician selects one of the icons in the task bar 202 to execute a function necessary for the clinical system. Note that the selection of icon in the task bar 202 is made by using a mouse cursor, or may be made by touching an icon through a touch panel provided on the display surface of the display device.

The task bar 202 has the navigation program icon 203. If the expert laboratory technician operating the clinical system cannot operate the system by himself/herself in a long period, or the technician is to go home, the technician selects the navigation program icon 203 such that a doctor or nurse unskilled in the operation of the clinical system can perform an urgent test in accordance with operation guidance by a navigation function. By the selection, the display screen of the display device turns to the initial screen 301 which is displayed in the case of operation by doctor or nurse unskilled in the operation of the clinical system, as shown in FIG. 3. The doctor or nurse unskilled in the operation must start the operation from this initial screen 301 and performs tests on samples in accordance with the operation guidance.

In the initial screen 301 as shown in FIG. 3, the operation menu 302 and the "back to initial screen" button 303 are displayed on the left side, and the title 305 having the process "start" button 306 is displayed at the center of the display screen. In this example, as the title 305, "Quick Response Lab. Navigation" is displayed. Further, in the initial screen 301, the "quit navigation" button 304 is displayed in its lower right position.

In the initial screen 301, the contents displayed in the operation menu 302 are numerals 1 to 5 indicating the order of sample testing and contents, "1 confirmation of sample", "2 confirmation of request", "3 feeding samples", "4 confirmation of result", and "5 finish". As described later, the operator selects the "start" button 306 to sequentially call display images as guidance on respective works, and performs operations in accordance with the guidance, thereby performs test on the sample. Further, the guidance on arbitrary work can be provided by selecting one of the items in the operation menu. The "back to initial screen" button 303 is an operation button to return to the initial screen as shown in FIG. 3. In this example, the button is inactivated. Further, the "quit navigation" button 304 is a button to return to the initial screen 201 displayed on the display device when the expert laboratory technician operates the clinical system. The "quit navigation" button 304 is effective only when the selection is made by the expert laboratory technician. That is, when the "quit navigation" button 304 is operated, a window (not shown) advising the user to input a password or the like is displayed, and only if the password that the expert laboratory technician knows is inputted, the "quit navigation" button 304 becomes effective, and the image returns to the initial screen 201. This arrangement prevents an operation error by a doctor or nurse unskilled in the operation to return to the initial screen of difficult operation as shown in FIG. 2.

Figure 4:
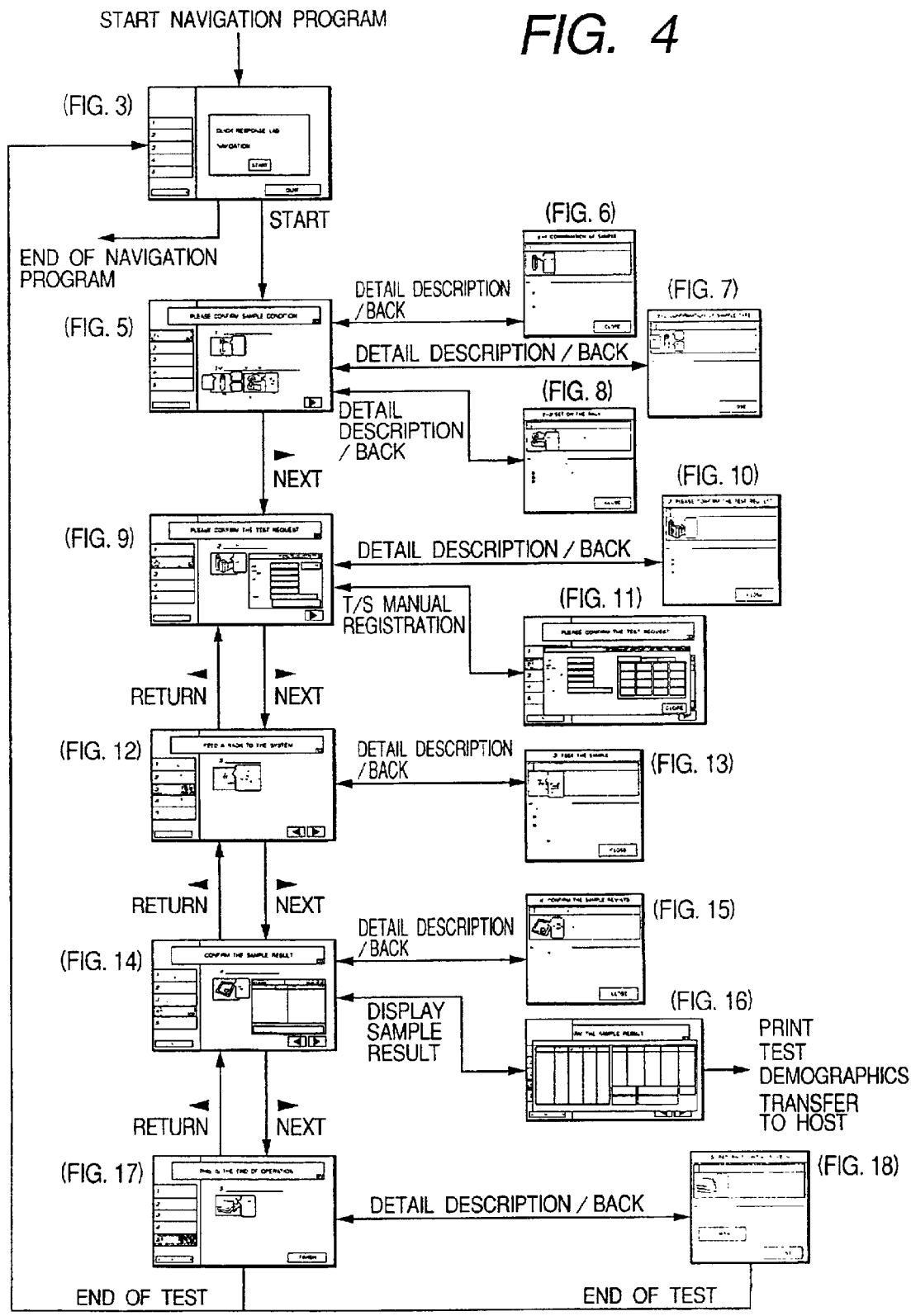
FIG. 4 is a flowchart showing an operation to perform a test on a sample in accordance with operation guidance of the clinical system according to an embodiment of the present invention using examples of display images.

FIG. 4 is a flowchart showing the operation to perform a test on a sample in accordance with operation guidance of the clinical system according to the embodiment of the present invention using examples of display images. FIGS. 5 to 18 are examples of operation guidance display images. Note that in FIGS. 5 to 18, the display images in FIGS. 5, 9, 12, 14 and 17 correspond to the respective items of the operation menu in the display image in FIG. 3, and the other display images are examples of display images of ancillary information as guidance on details of operation. The layout of the display image of these ancillary information to be described below is a standard layout, and in consideration of difference in attachment status of barcodes attached to sample containers by users, the layout may be customized by user.

Next, the operation in accordance with the flowchart of FIG. 4 will be described with reference to the display image examples in FIGS. 5 to 18.

(1) When a sample to be urgently tested is provided and a doctor or nurse unskilled in operation uses the clinical system to perform a test on the sample, the doctor or the like first selects the "start" button 306 in the initial screen 301 described in FIG. 3, displayed on the display device. The display turns to an image for sample confirmation as shown in FIG. 5.

Figure 5:
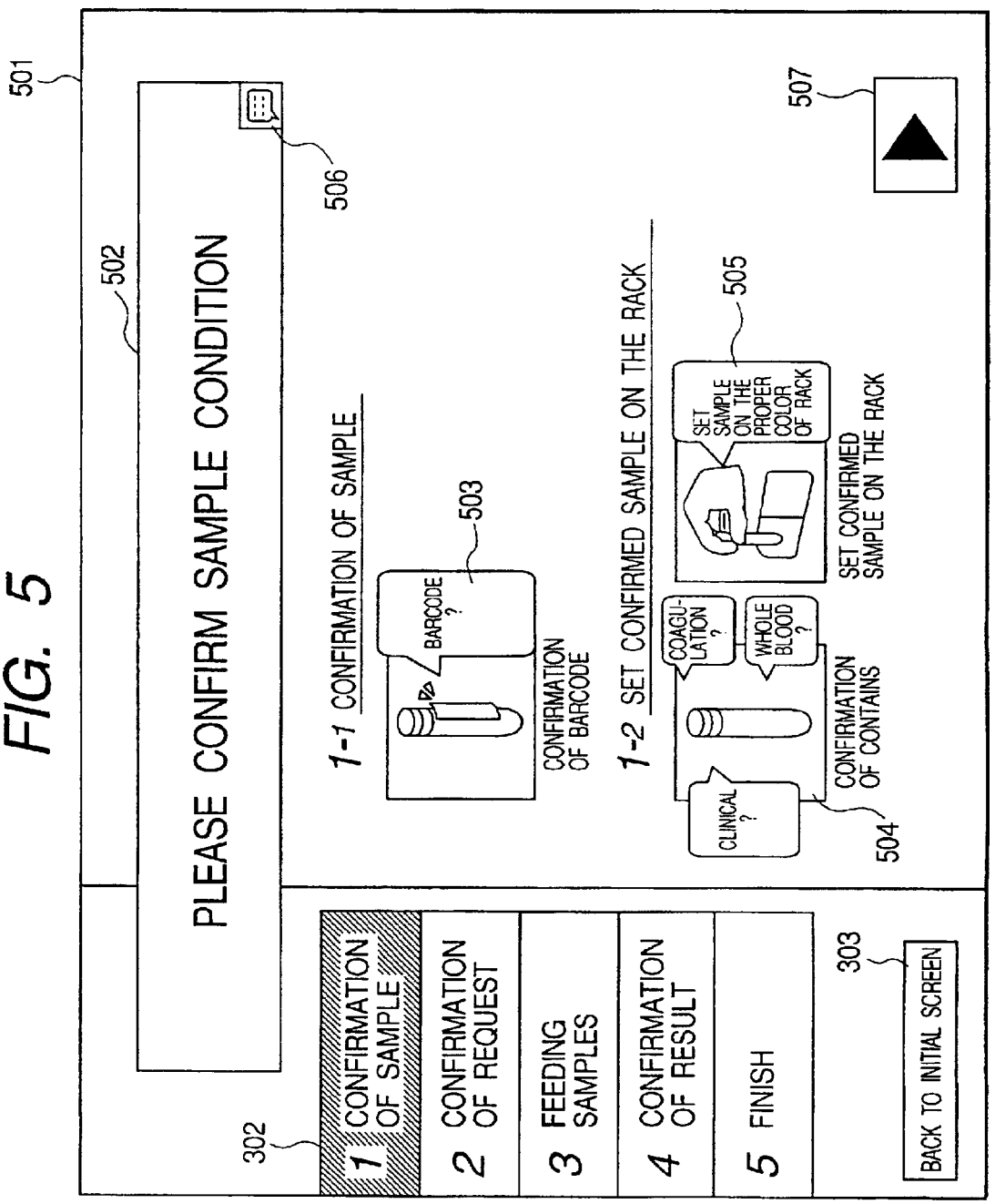
FIG. 5 is an example of operation guidance display image (1)

(2) FIG. 5 shows a display image 501 as an example of display image to confirm the sample before the sample is set on the rack 1 described in FIG. 1. A guidance title 502 "Please confirmation sample condition", a schematic illustration 503 as guidance on confirming a barcode attached to the sample, a schematic illustration 504 as guidance on confirming the contents of the sample, and a schematic illustration 505 as guidance on setting the confirmed sample on the rack 1 are displayed. These schematic illustrations indicate the outlines of the works, and also function as icons to display details of these guidances to call ancillary information display images explaining detailed information, as described later. Further, in the display image, a "next" button 507 to move to the next image is displayed, and a "voice output" button 506 is displayed in the position of the guidance title 502. As the display image 501 is displayed for sample confirmation, the "1 confirmation of sample" button in the operation menu is inactive, and the "back to initial screen" button 303 is active.

When the display image changes to the image in FIG. 5 by the selection of the "start" button 306 in the initial screen 301 described in FIG. 3, details of sample confirmation are explained for respective items by voice. The doctor or nurse as the operator, who has completed the sample confirmation only by this display image, can move to the display image for order check by the "next" button 507. On the other hand, when the operator desires to know the details of sample confirmation, the operator selects the schematic illustrations 503 to 505 as guidance which also function as icons. Further, if the operator selects the "voice output" button 506, the details of the sample confirmation are explained again by voice. In the present embodiment, only information on the outline of work as important information of test is displayed on the main window for operation guidance, such that operation guidance is visually easily understood and errors can be reduced. Further, as detailed information is displayed in a sub window, information can be selected in accordance with the operator's experience. Further, as the detailed information is outputted as voice guidance, the operator's auditory sense besides the visual sense is utilized for improvement in work accuracy.

Figure 6:
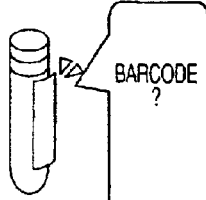
FIG. 6 is an example of operation guidance display image (2)

(3) Assuming that the schematic illustration 503 in the guidance in the display image in FIG. 5 is selected now, the display changes to a display image 601 as shown in FIG. 6. The display image 601, displayed for barcode check, guides the operator by using schematic illustration to confirm presence/absence of sample barcode and confirm whether the barcode is attached to a proper position or not. Further, particular ways of confirming are explained by sentences. The operator can properly attach the barcode to the sample by the explanatory sentences. Then the operator selects a "close" button 602, and the display returns to the display image in FIG.

Figure 7:
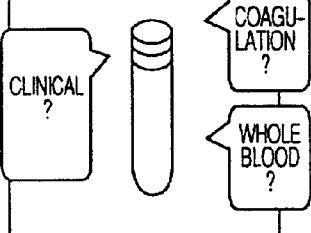
FIG. 7 is an example of operation guidance display image (3)

(4) Further, if the schematic illustration 504 as guidance in the display image in FIG. 5 is selected, the display changes to a display image 701 as shown in FIG. 7. The display image 701, displayed for confirming the content of the sample, guides the operator by using schematic illustration to confirm the type of sample as, e.g., sample for biochemical test, sample for coagulation test, or sample for blood test. Further, a particular way of confirming is explained by sentences. The operator can confirm the content of the sample by the display image 701 in FIG. 7. Then the operator selects a "close" button 702, and the display returns to the initial screen in FIG. 5.

Figure 8:
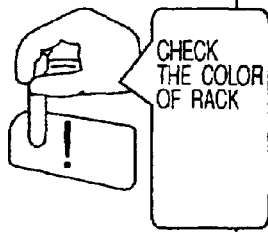
FIG. 8 is an example of operation guidance display image (4)

(5) Further, if the schematic illustration 505 as guidance in the display image in FIG. 5 is selected, the display changes to a display image 801 as shown in FIG. 8. The display image 801, displayed for setting the sample on a corresponding rack in accordance with the type of sample confirmed by using the image in FIG. 7, guides the operator by using schematic illustration to set the sample on a rack in a color corresponding to the type of sample. Further, particular ways of setting of sample to a rack in a corresponding color are explained by sentences. The operator can properly sets the sample on the rack by the explanatory sentence. Then the operator selects a "close" button 802, and the display returns to the display image in FIG. 5.

Note that in the guidance by the image examples in FIGS. 6 to 8, voice guidance may be performed as in the case of FIG. 5.

Figure 9:
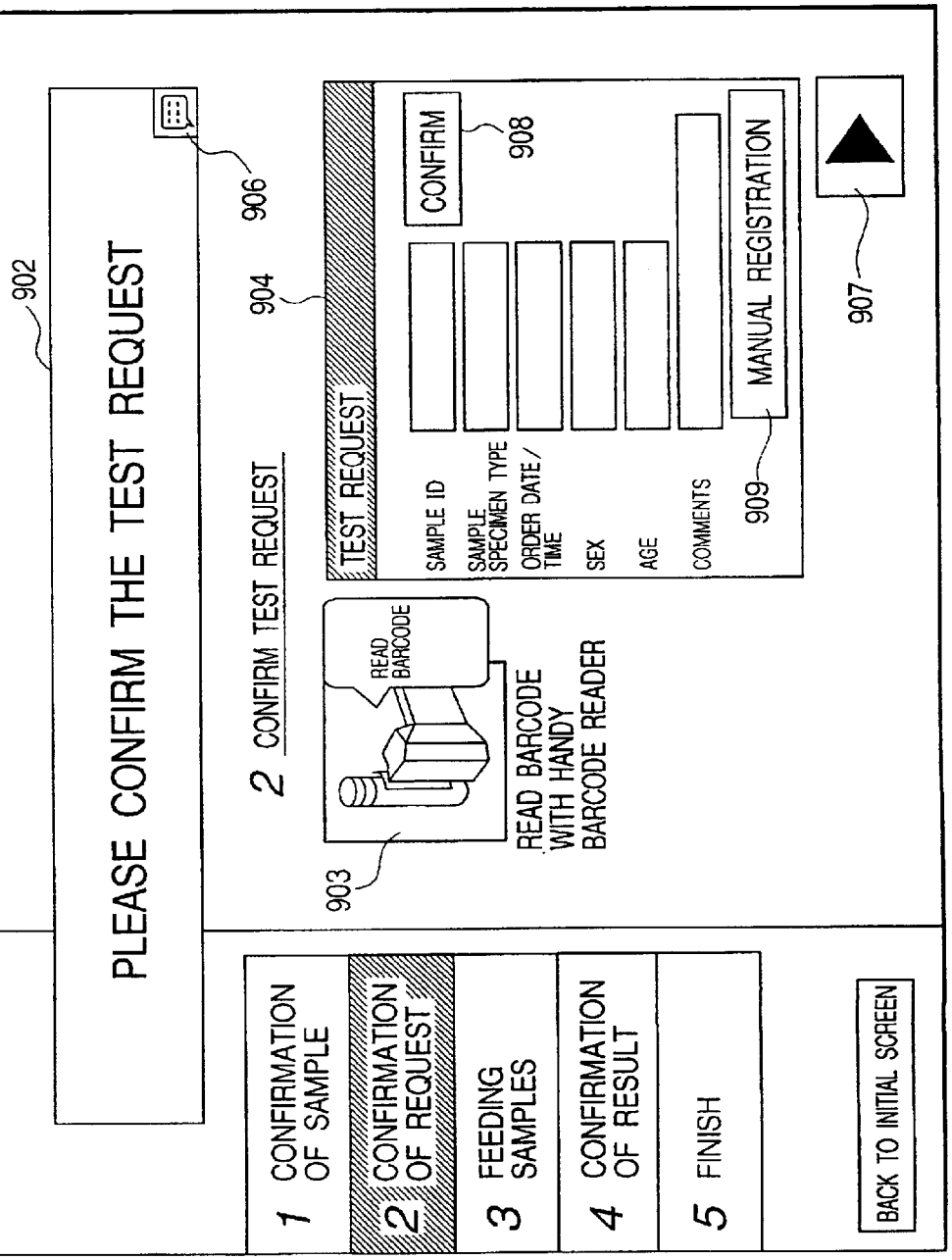
FIG. 9 is an example of operation guidance display image (5)

(6) The doctor or nurse as the operator, who has confirmed the sample by the display image described in FIG. 5 or the guidance of the display images described in FIGS. 6 to 8, selects the "next" button 507. Then, the display changes to a display image 901 as shown in FIG. 9 to confirm the contents of order. The display image 901 is an example of display image to guide the operator to read the barcode attached to the sample after the sample has been set or before the sample is set on the rack 1 described in FIG. 1, and to confirm the contents of the order. A guidance title 902 "Please confirm the test request", a schematic illustration 903 as guidance on reading the barcode attached to the sample, and a window 904 to display the read contents of the order, are displayed in the display image 901. The schematic illustration 903 also functions as an icon to display details of the guidance as described later. Further, in the display image, a "next" button 907 to move to the next image is displayed, and a "voice output" button 906 is displayed in the position of the guidance title 902. Further, a "confirm" button 908 in which the operator inputs that the contents of order have been confirmed, and a "manual registration" button 909 in which the operator inputs start of manual registration if a part of contents of order is missing, for example, are displayed in the window 904. As the display image 901 is displayed for order check, the order check button in the operation menu is inactive.

Then, when the display changes to the image in FIG. 9, the way to confirm the contents of the order is explained by voice. The doctor or nurse as the operator, who has confirmed the contents of the order by the display image, can move to the next display image to set the sample by selection of the "next" button 907. On the other hand, if the operator desires to know the details of confirming of the contents of order, the operator can obtain the details by selecting the schematic illustration 903 that also functions as an icon. Further, if the operator selects the "voice output" button 906, the way to confirm the contents or order is explained again by voice.

Figure 10:
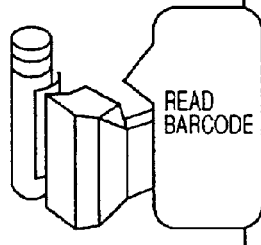
FIG. 10 is an example of operation guidance display image (6)

(7) If the schematic illustration 903 as guidance in the display image in FIG. 9 is selected, the display changes to a display image 1001 as shown in FIG. 10. The display image 1001 is displayed as guidance on reading the barcode attached to the sample and to confirm the read items of order. In this example, the way to read the barcode is guided by the schematic illustration. Further, troubleshooting guidance upon occurrence of trouble, e.g., when no item of order found, is explained by sentences. The operator can properly read the barcode of the sample and checks it by the explanatory sentences. Then the operator selects a "close" button 1002, and the display image returns to the display image in FIG. 9.

Figure 11:
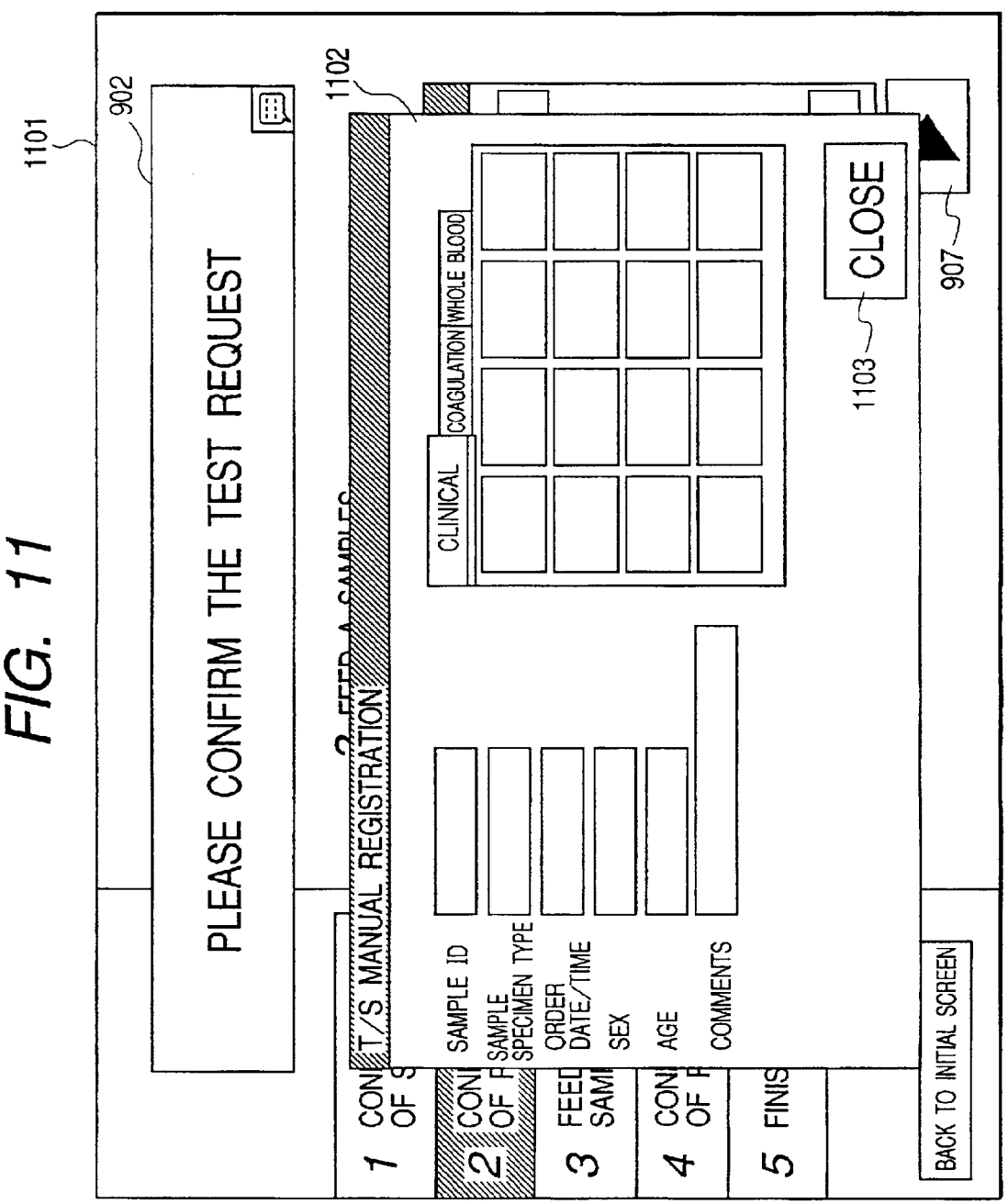
FIG. 11 is an example of operation guidance display image (7)

(8) If the "manual registration" button 909 is selected in the window 904 displaying the contents of order shown in FIG. 9, the display changes to a display image 1101 as shown in FIG. 11. The display image 1101 is displayed to guide the operator to manually input contents of order which have not been described in the barcode or have not been read from the barcode. An input window 1102 is opened on the display image in FIG. 9. The operator inputs necessary information in this image from an input device such as a keyboard, and when the operator selects a "close" button 1103, the display image returns to the display image in FIG. 9. The window 904 displaying the contents of order in FIG. 9 is updated with the input information.

Also in the guidance by the images in FIGS. 10 and 11, voice guidance may be performed as in the case of FIG. 9.

Figure 12:
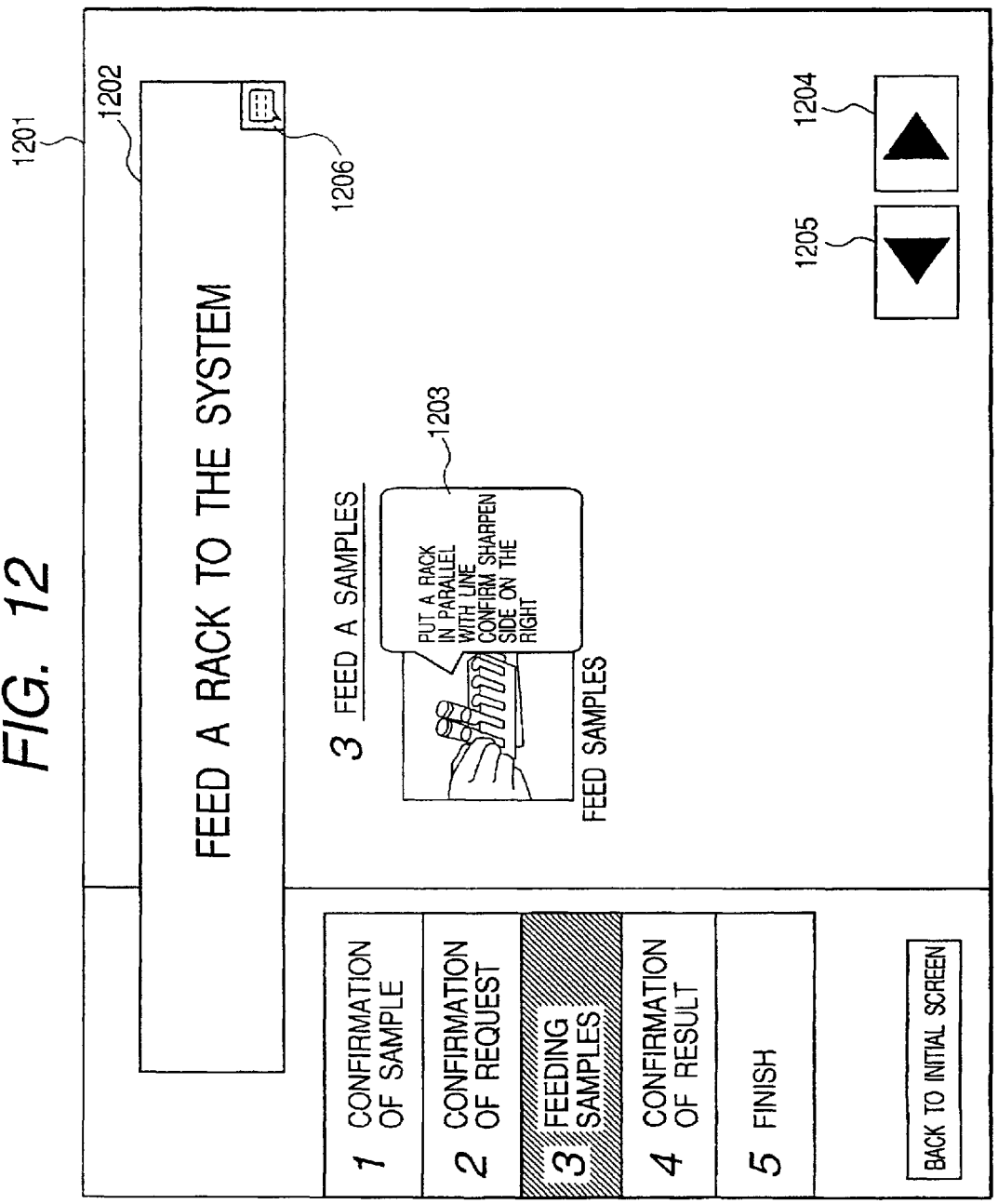
FIG. 12 is an example of operation guidance display image (8)

(9) When the operator confirms the contents of order in the window 904 showing the contents of order in FIG. 9, then selects the "confirm" button 908 and select the "next" button 907, the display changes to a display image 1201 as shown in FIG. 12 as guidance on sample setting. The display image 1201 is displayed as guidance on forwarding the rack 1 where the sample is set to the clinical system. A guidance title 1202 "Feed a rack to the system", a schematic illustration 1203 showing the way to set the rack, a "next" button 1204 and a "return" button 1205 are displayed. The schematic illustration 1203 of the above guidance also functions as an icon to display details of the guidance as described later. As the display image 1201 is displayed to set the sample in the system, the "3 feeding samples" button in the operation menu is inactive.

When the display changes to the image as shown in FIG. 12, the way to set the sample in the system is explained by voice. The doctor or nurse as the operator, who has confirmed the contents of order only by the display image, can move to the next display image to confirm test result by the "next" button 1204. On the other hand, if the operator desires to know the details of sample setting, the operator can obtain the details by selecting the schematic illustration 1203 that also functions as an icon. Further, if the operator selects a "voice output" button 1206, the way to set the sample in the system is explained again by voice. Further, if the operator selects the "return" button 1205, the display returns to the display image to confirm the contents of order described in FIG. 9.

(10) When the schematic illustration 1203 as guidance is selected in the display image in FIG. 12, the display moves to a display image 1301 as shown in FIG. 13. The display image 1301 is displayed as guidance on setting the rack where the sample is set into the system. In this example, the display image shows the way to set the rack in the system by schematic illustration. Further, the detailed procedure of setting is explained by sentences. The operator can properly set the rack where the sample is set in the system in accordance with the explanatory sentences. Then, the operator selects a "close" button 1302, and the display image returns to the display image in FIG. 12. Note that the guidance here may be made as voice guidance.

Figure 14:
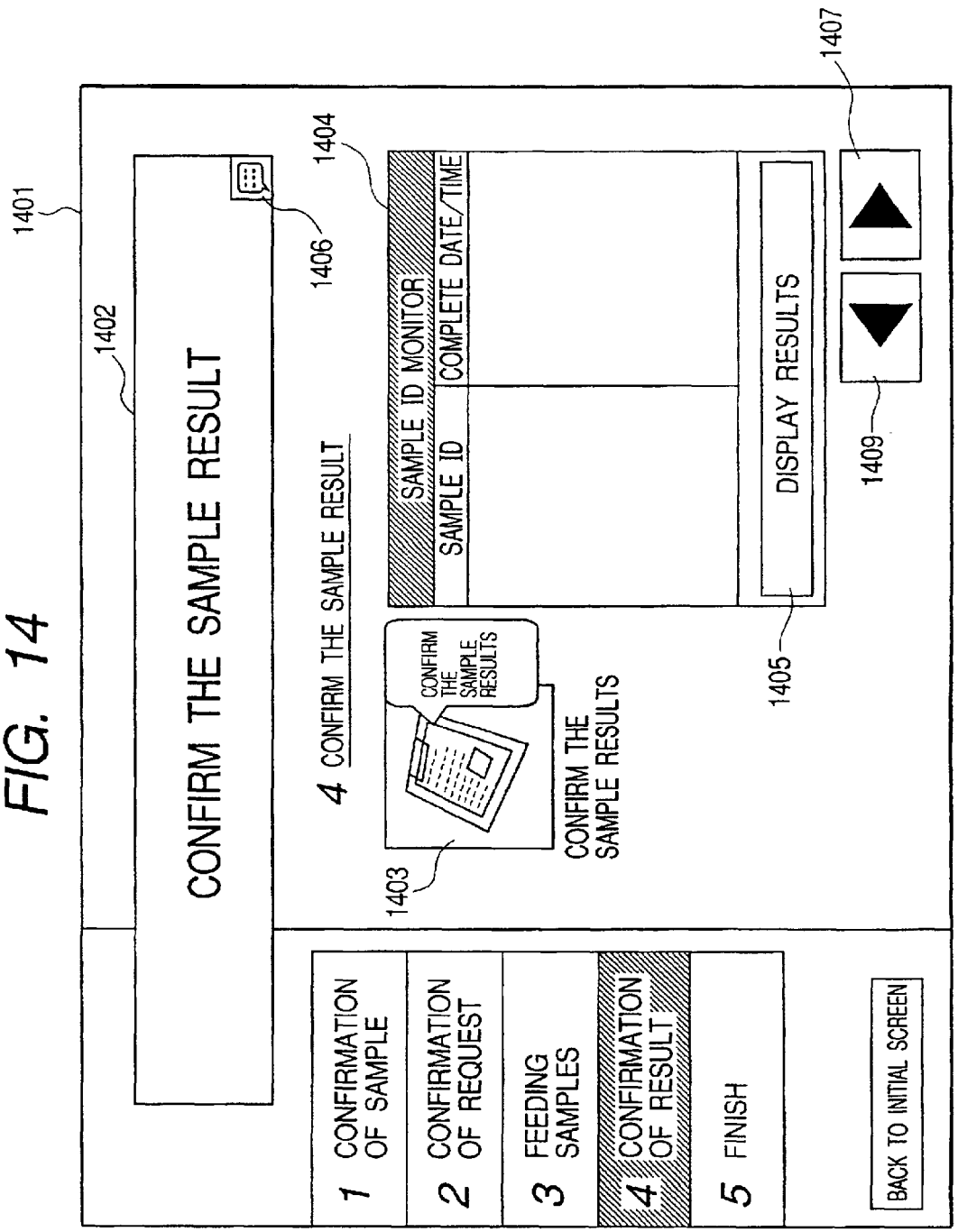
FIG. 14 is an example of operation guidance display image (10)

(11) The doctor or nurse as the operator, who has set the sample by the guidance of the display image described in FIG. 12 or referring to the display image described in FIG. 13, selects the "next" button 1204. Then the display changes to a display image 1401 as shown in FIG. 14 to confirm the result of test of the sample. Note that it may be arranged such that the doctor or nurse can see the test result from other place than the clinical laboratory. The display image 1401 is displayed for confirming the result of test by the clinical system described in FIG. 1. A guidance title 1402 "Confirm the sample result", a schematic illustration 1403 as guidance on confirming the test result, and a window 1404 displaying the contents of test result are displayed. The schematic illustration 1403 also functions as an icon to display the details of guidance as described later. Further, in the display image, a "next" button 1407 to move to the next image and a "return" button 1408 to return to the display image described in FIG. 12 are displayed, and a "voice output" button 1406 is displayed in the position of the guidance title 1402. Further, a result display 1405 to display the contents of test result is displayed in the window 1404. As the display image 1401 is displayed for confirming the result of test on the sample, the "4 confirmation of result" button in the operation menu is inactive.

Then, when the display changes to the image as shown in FIG. 14, the way to confirm the result is explained by voice. The doctor or nurse as the operator, who has confirmed the contents of the order only by the display image, can move to the next display image for sample setting operation by the "next" button 1407, while return to the display image described in FIG. 12 by selecting the "return" button 1409. On the other hand, if the operator desires to know the way to confirm the test result, the operator can obtain the details of the way to confirm the test result by selecting the schematic illustration 1403 that also functions as an icon. Further, if the operator selects the "voice output" button 1406, the way to confirm the test result is explained again by voice.

Figure 15:
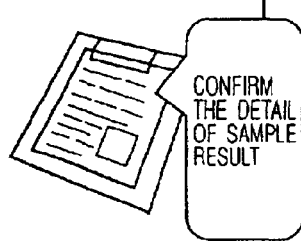
FIG. 15 is an example of operation guidance display image (11)

(12) If the schematic illustration 1403 as guidance is selected in the display image in FIG. 14, the display changes to a display image 1501 as shown in FIG. 15. The display image 1501, displayed as guidance on confirming the result of test on the sample, guides the operator to confirm the result by schematic illustration. Further, the way to confirm the test result is explained by sentences. The operator can properly confirm the result by the explanatory sentences. Then the operator selects a "close" button 1502, then the display image returns to the display image in FIG. 14. Note that the guidance here may be made by voice guidance.

Figure 16:
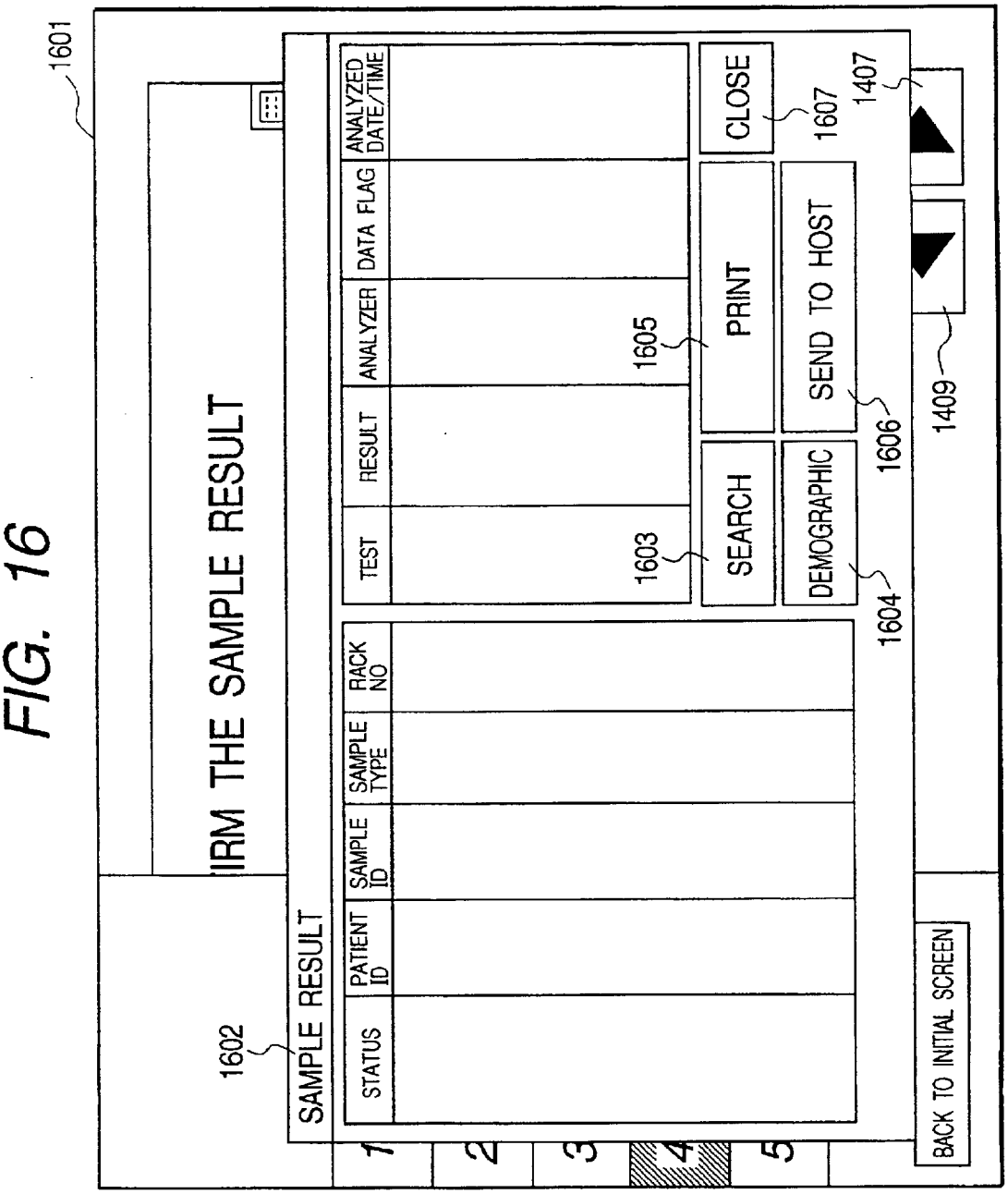
FIG. 16 is an example of operation guidance display image (12)

(13) If the "display results" button 1405 is selected in the window 1404 showing the acquisition of test result as shown in FIG. 14, the display changes to a display image 1601 as shown in FIG. 16. As the display image 1601, a window 1602 showing the test result is opened on the display image in FIG. 14. The operator can confirm the test result by the image. In the window 1602, a "search" button 1603, an "demographic" button 1604, a "print report" button 1605, a "send to HOST" button 1606, and a "close" button 1607 are displayed, and respective processings are executed by selecting one of the "search" button 1603, the "demographic" button 1604, the "print report" button 1605 and the "send to HOST" button 1606. Further, if the "close" button 1607 is selected, the display image returns to the display image in FIG. 14.

Figure 17:
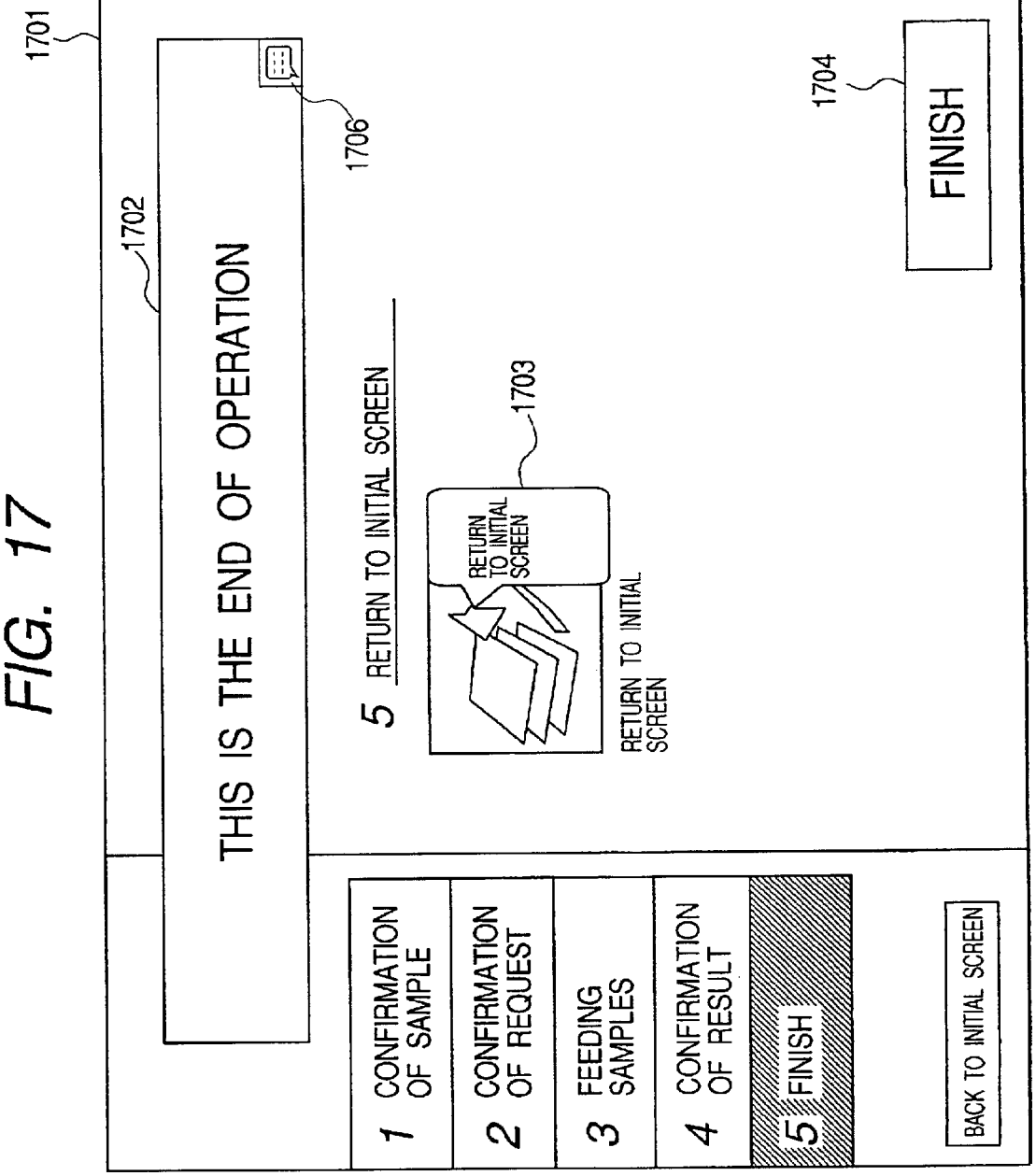
FIG. 17 is an example of operation guidance display image (13)

(14) The doctor or nurse as the operator, who has confirmed the test result by the guidance of the display image described in FIG. 14 or referring to the display images described in FIGS. 15 and 16, selects the "next" button 1407. Then the display changes to a display image 1701 as shown in FIG. 17 for termination of the processing. The display image 1701 is displayed to return to the initial screen and to terminate the processing since the test by the clinical system has been completed. A guidance title 1702 "This is the end of operation. Terminate processing", a schematic illustration 1703 as guidance on termination of the processing, and a "finish" button 1704 are displayed. The schematic illustration 1703 showing the guidance also functions as an icon to display the details of the guidance as described later. Further, a "voice output" button 1706 is displayed in the position of the guidance title 1702. As the display image 1701 is displayed for termination of the operation, the "5 finish" button in the operation menu is inactive.

Then, when the display changes to the image in FIG. 17, the way to terminate the operation is explained by voice. The doctor or nurse as the operator, who has known the way to terminate the operation only by display image, can move to the initial screen described in FIG. 3 by selecting the "finish" button 1704, thus all the processing is terminated. On the other hand, if the operator desires to know the details of the way to complete the operation, the operator can obtain the details by selecting the schematic illustration 1703 that also functions as an icon. Further, if the operator selects the "voice output" button 1706, the way to confirm the test result is explained again by voice.

Figure 18:
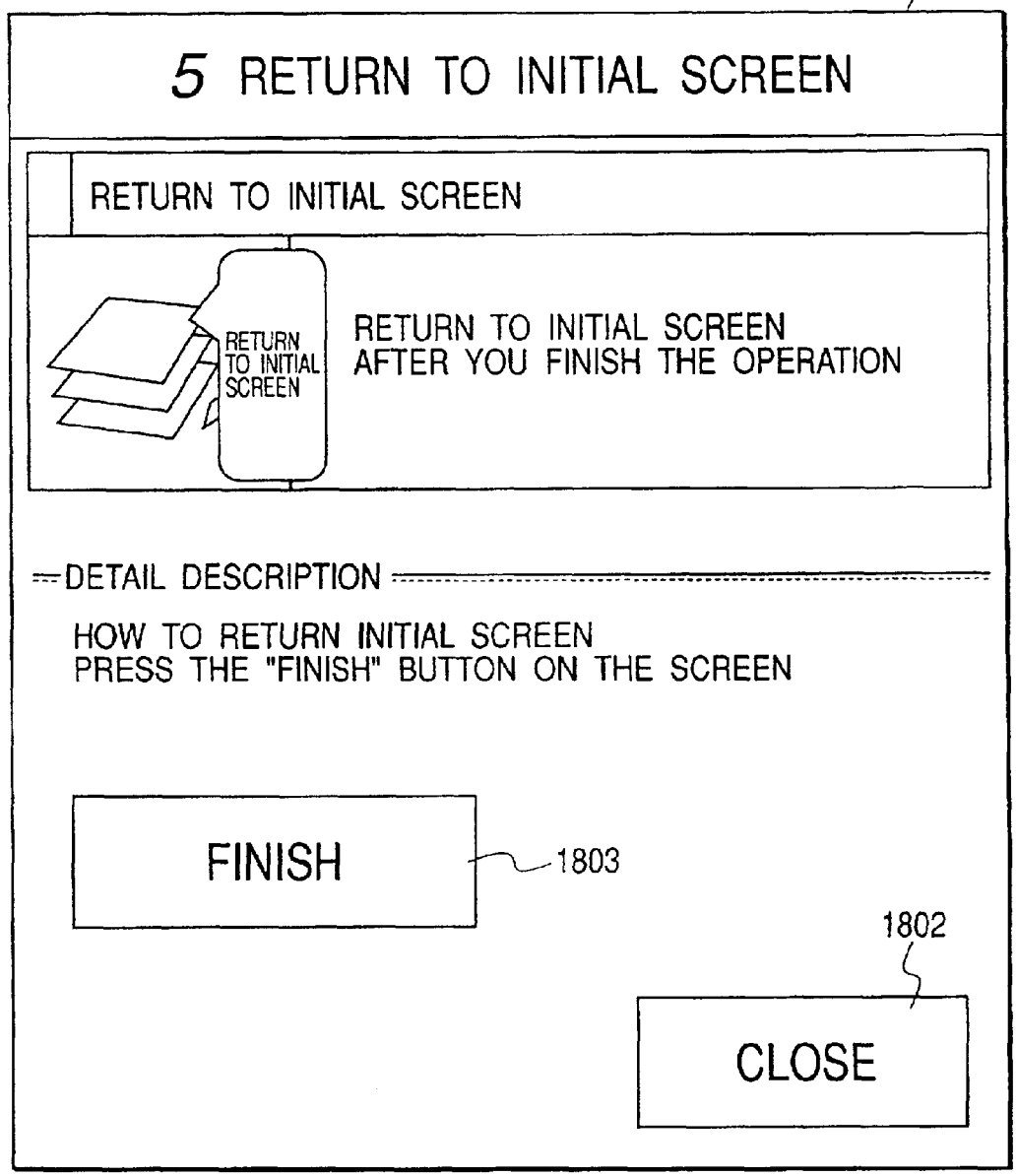
FIG. 18 is an example of operation guidance display image (14).

(15) If the schematic illustration 1703 is selected in the display image in FIG. 17, the display changes to a display image 1801 as shown in FIG. 18. The display image 1801, displayed as guidance on termination of the processing by completion of operation, guides the operator to terminate the processing by schematic illustration. Further, the detailed explanation of process procedure is made by sentences. The operator can properly terminate the processing by the explanatory sentences. Then the operator selects a "close" button 1802, and the display image returns to the display image in FIG. 17. Further, if a "finish" button 1803 is selected, the display image directly moves to the initial screen described in FIG. 3. Note that the guidance here may be made by voice.

In the embodiment of the present invention as described above, the operation guidance is made in the order of works in the operation menu, however, it may be arranged such that when the operation menu is displayed on the display image, an arbitrary work is selected and guidance of the work is received. In time, regarding some works and confirming, even an unskilled operator like a doctor or nurse will be accustomed to operation and can proceed with processing without error without guidance. In such case, the operator can perform processing efficiently.

As described above, according to the present invention, in the case where an expert laboratory technician is absent and a clinical system is operated by an unskilled doctor or nurse, operation guidance can be made for operating the clinical system without operation error.

What is claimed is:

1. An operation guidance method of a clinical system for testing biological samples, wherein a display image is switched over between a first mode where a display image is for a laboratory technician, and a second mode where a display image is for a non-laboratory-technician and operation guidance is displayed as a navigation function, wherein said method in the second mode comprises:

sorting out works to be performed by the non-laboratory-technician with guidance in accordance with a procedure of operation normally performed by said laboratory technician;

displaying a menu of sorted works on an initial screen;

providing guidance on operation by sequentially displaying display images as operation guidance on respective works in accordance with said procedure of operation;

displaying one or a plurality of schematic operation guidance illustrations in said display images as operation guidance;

selecting an operation guidance illustration and displaying a display image of ancillary information to further explain said operation guidance illustration as selected.

2. The operation guidance method of a clinical system according to claim 1, wherein said schematic operation guidance illustrations are displayed in a task bar with icons, and upon selecting any one of said icons, said display image of ancillary information is displayed to further explain said icon as selected.

3. The operation guidance method of a clinical system according to claim 1, wherein said display image of ancillary information is customizable by a user.

4. The operation guidance method of a clinical system according to claim 1, wherein when said schematic operation guidance illustrations are displayed, details of said operation guidance illustrations are explained by voice.

5. The operation guidance method of a clinical system according to claim 1, wherein when said display image of ancillary information is displayed, detailed operation guidance is made by voice.

6. The operation guidance method of a clinical system according to claim 5, wherein said operation guidance by voice is made at an arbitrary time by selection of a voice reproduction button displayed in the display image.

7. The operation guidance method of a clinical system according to claim 1, wherein said display image is switched over between said first mode and said second mode by selection of an icon in a task bar that is operable only by the laboratory technician.

8. The operation guidance method of a clinical system according to claim 1, wherein said display image is selectably lockable to said second mode to restrict the non-laboratory-technician to the second mode.

9. An operation guidance method of a clinical system for testing biological samples, wherein a display image is switched over between a first mode where a display image is for a laboratory technician, and a second mode where a display mode is for a non-laboratory-technician and operation guidance is displayed as a navigation function, wherein said method in the second mode comprises:

sorting out works to be performed by the non-laboratory-technician in accordance with a procedure of operation normally performed by said laboratory technician;

displaying a menu of sorted works on an initial screen;

selecting one of the works from said menu and, displaying a display image as guidance on the work;

displaying one or a plurality of schematic operation guidance illustrations in said display image as operation guidance;

selecting an operation guidance illustration and displaying a display image of ancillary information to further explain said operation guidance illustration as selected.

10. The operation guidance method of a clinical system according to claim 9, wherein said display image is selectably lockable to said second mode to restrict non-laboratory-technician to the second mode.

11. An operation guidance method of a clinical system for testing biological samples, wherein a display image is switched over between a first mode where a display image is for a laboratory technician, and a second mode where a display image is for a non-laboratory-technician and operation guidance is displayed as a navigation function, wherein said method in the second mode comprises:

sorting out works to be performed by the non-laboratory-technician in accordance with a procedure of operation normally performed by said laboratory technician;

displaying a menu of sorted works on an initial screen; and providing guidance on operation by sequentially displaying display images as operation guidance on respective works in accordance with said procedure of operation, wherein said display images as operation guidance include one or a plurality of schematic operation guidance illustrations, and said operation guidance illustrations are selectable, so that upon selecting any one of said illustrations, a display image of ancillary information is displayed to further explain said operation guidance illustration as selected, and wherein, when a display image of a first sorted work is displayed as operation guidance, operation guidance to the next sequential sorted works continued by selecting a check button displayed in the display image of the first sorted work.

12. The operation guidance method of a clinical system according to claim 11, wherein said display image is selectably lockable to said second mode to restrict the non-laboratory-technician to the second mode.

* * * * *